(12) United States Patent
Marion et al.

(10) Patent No.: US 9,416,142 B2
(45) Date of Patent: Aug. 16, 2016

(54) GRISEOFULVIN DERIVATIVES

(71) Applicant: PIERRE FABRE MEDICAMENT, Boulogne-Billancourt (FR)

(72) Inventors: Frédéric Marion, Toulouse (FR); Frédéric Lieby-Muller, Portet-sur-Garonne (FR); Serge Grisoni, Portet-sur-Garonne (FR); Emmannuel Fournier, Muret (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/418,728

(22) PCT Filed: Aug. 1, 2013

(86) PCT No.: PCT/EP2013/066169
§ 371 (c)(1),
(2) Date: Jan. 30, 2015

(87) PCT Pub. No.: WO2014/020105
PCT Pub. Date: Feb. 6, 2014

(65) Prior Publication Data
US 2015/0191443 A1    Jul. 9, 2015

(30) Foreign Application Priority Data

Aug. 1, 2012   (FR) ..................... 12 57482

(51) Int. Cl.
| | | |
|---|---|---|
| A61K 31/343 | (2006.01) | |
| C07D 307/94 | (2006.01) | |
| C07D 495/10 | (2006.01) | |
| C07D 405/14 | (2006.01) | |
| C07D 405/12 | (2006.01) | |
| C07D 407/04 | (2006.01) | |
| C07D 407/12 | (2006.01) | |
| C07D 409/04 | (2006.01) | |
| C07D 491/107 | (2006.01) | |
| C07D 493/10 | (2006.01) | |

(52) U.S. Cl.
CPC ............ C07D 495/10 (2013.01); C07D 307/94 (2013.01); C07D 405/12 (2013.01); C07D 405/14 (2013.01); C07D 407/04 (2013.01); C07D 407/12 (2013.01); C07D 409/04 (2013.01); C07D 491/107 (2013.01); C07D 493/10 (2013.01)

(58) Field of Classification Search
CPC ........................... A61K 31/343; C07D 307/94
USPC .......................................... 549/345; 514/462
See application file for complete search history.

(56) References Cited

U.S. PATENT DOCUMENTS 9,108,941 B2 * 8/2015 Kraemer ............. C07D 307/94

FOREIGN PATENT DOCUMENTS

| EP | 2 008 652 A1 | 12/2008 |
| EP | 2 204 367 A1 | 7/2010 |

OTHER PUBLICATIONS

Birch et al., "Studies in Relation to Biosynthesis. Part XIII.* Griseofulvin.", J. Chem. Soc., Jan. 1, 1958, pp. 360-365.
Caesar Accession No. 1431, Lesniewska et al., "Transformations of griseofulvin in strong acidic conditions—crystal structures of 2'-demethylgriseofulvin and dimerized griseofulvin", Natural Product Communications, vol. 7, No. 3, 2012, 1 page, XP-002694255.
Gregory et al., "Griseofulvin Analogues. Part II. Some 3'-Alkyl-griseofulvic Acids and Their Enol. Ethers.", J. Chem. Soc., 1962, pp. 1269-1276, XP009117842.
International Preliminary Report on Patentability and Written Opinion of the International Searching Authority (Forms PCT/IB/373 and PCT/ISA/237)and English translation thereof, dated Feb. 3, 2015, for International Application No. PCT/EP2013/066169.
International Searching Report (PCT/ISA/210) and English translation thereof, dated Oct. 16, 2013, for International Application No. PCT/EP2013/066169.
Lesniewska et al., "Transformations of griseofulvin in strong acidic conditions—crystal structures of 2'-demethylgriseofulvin and dimerized griseofulvin", Natural Product Communications, vol. 7, No. 3, 2012, pp. 327-332, XP-008160903.
Mir et al., "Correlation between the In Vivo Effects of some Griseofulvin Derivatives and their In Vitro Interactions with Mammalian Microtubules", FEBS Letters, vol. 88, No. 2, Apr. 1978, pp. 259-263.

(Continued)

*Primary Examiner* — Golam M M Shameem
(74) *Attorney, Agent, or Firm* — Birch, Stewart, Kolasch & Birch, LLP.

(57) ABSTRACT

The present invention relates to compounds of the following general formula (I), or to a pharmaceutically acceptable salt thereof, as well as to the uses thereof as a drug, in particular for treating cancerous or precancerous hyperproliferative conditions, and to the pharmaceutical compositions containing same.

6 Claims, No Drawings

(56) References Cited

OTHER PUBLICATIONS

Newman, "Epoxidation of Griseofulvin. A New Reaction of the β-Methoxyenone System", J. Org. Chem., vol. 35, No. 11, 1970, pp. 3990-3993, XP55057107A.
Oda et al., "Regio- and Stereoselective Hydrogenation of 2'-Demethoxy-2'-methyldehydrogriseofulvin, a Symmetrical Substrate, to (+)-2'Demethoxy-2'-methylgriseofulvin with a Cell-Free System . . . ", Chem. Pharm. Bull., vol. 38, No. 2, Feb. 1990, pp. 525-528, XP55057104A.
Panda et al., "Kinetic suppression of microtubule dynamic instability by griseofulvin: Implications for its possible use in the treatment of cancer", PNAS, vol. 102, No. 28, Jul. 12, 2005, pp. 9878-9883.
Rebacz et al., "Identification of Griseofulvin as an Inhibitor of Centrosomal Clustering in a Phenotype-Based Screen", Cancer Research, vol. 67, No. 13, Jul. 1, 2007, pp. 6342-6350.
Rønnest et al., Synthesis and Structure—Activity Relationship of Griseofulvin Analogues as Inhibitors of Centrosomal Clustering in Cancer Cells, J. Med. Chem., vol. 52, No. 10, 2009 (Published online Apr. 29, 2009), pp. 3342-3347.
Yamato et al., "An Improved Synthetic Method for dl-Griseofulvin and Its 2'-S-Analogue", Papers, Jul. 1990, pp. 569-570, XP55082492A.

* cited by examiner

GRISEOFULVIN DERIVATIVES

The present invention relates to derivatives of griseofulvin and to the use thereof for the treatment of cancerous and pre-cancerous hyperproliferative pathologies.

Griseofulvin 1 is a natural molecule isolated from cultures of filamentous fungi *Penicilium griseofulvum* [*J. Chem. Soc.* 1958, 360-365]. It is used in the treatment of fungal skin disorders in human and is also used in veterinary medicine. It is chiefly given via oral route at doses of 0.5 to 1.0 gram per day in human.

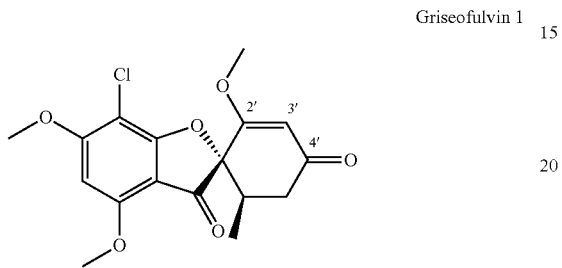

Griseofulvin 1

While the mechanism of action of griseofulvin on fungi still remains ill understood, several studies indicate possible involvement in perturbation of the microtubular network [*FEBS Letters* 1978, 259-263; *PNAS* 2005, 978-9883; *Cancer Res.*, 2007, 6342-6350] in eukaryote cells to explain its low cytotoxicity and anti-cancer potential.

With a view to improving the anti-tumour properties of griseofulvin, derivatives of griseofulvin substituted at 2' with oxygen- or sulfur-containing groups [*J. Med Chem.* 2009, 3342-3347] have been synthesised. However none of these products has displayed sufficient potential for use as drug to treat cancerous and pre-cancerous hyperproliferative pathologies.

The inventors have surprisingly discovered that the adding of particular groups at 2' and/or 3' allows the obtaining of cytotoxic derivatives that are more powerful than griseofulvin and its previously described analogues, and having remarkable activity on cancer lines particularly resistant to known cytotoxics.

The subject of the present invention is therefore a compound of following general formula (I):

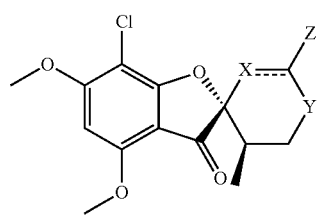

(I)

or a pharmaceutically acceptable salt thereof,
where:
  ---- represents a single or double bond;
  Y is C=O, C=S, CH$_2$, CH—OR$_1$, CHN$_3$, CHNR$_2$R$_3$, C=N—OR$_4$, C=N—NR$_5$R$_6$, advantageously a C=O or CH—OR$_1$ group; and
  either Z is a —S(O)R$_7$ or —S(O)$_2$R$_7$ group and X is a CH—R$_8$ group when ---- represents a single bond or C—R$_8$ when ---- represents a double bond;

or Z is a hydrogen atom or a R$_9$ group, and X is a CH—R$_{10}$ group when ---- represents a single bond or C—R$_{10}$ when ---- represents a double bond,
with:
  R$_1$ to R$_5$ each independently representing a hydrogen atom or a (C$_1$-C$_6$)alkyl, aryl, (C$_1$-C$_6$)alkyl-aryl, aryl-(C$_1$-C$_6$)alkyl or 5- or 6-membered heterocycle group;
  R$_6$ representing a hydrogen atom or a (C$_1$-C$_6$)alkyl, aryl, (C$_1$-C$_6$)alkyl-aryl, aryl-(C$_1$-C$_6$)alkyl, C(O)NH$_2$, C(S)NH$_2$ or 5- or 6-membered heterocycle group;
  R$_7$ representing a (C$_1$-C$_6$)alkyl, aryl, (C$_1$-C$_6$)alkyl-aryl, aryl-(C$_1$-C$_6$)alkyl or 5- or 6-membered heterocycle group;
  R$_8$ representing —R$_{11}$, —NHR$_{11}$, —CH$_2$—NHR$_{11}$, —CH$_2$—NH—C(O)—R$_{11}$, —NH—CH$_2$—R$_{11}$, —NH—NH—R$_{11}$, —NH—C(O)—R$_{11}$, —NH—C(O)—CH$_2$—R$_{11}$, —NH—CH$_2$—C(O)—R$_{11}$, —NH—CH$_2$—C(O)—O—R$_{11}$, —NH—CH$_2$—C(O)—NH—R$_{11}$, —NH—SO$_2$—R$_{11}$, —S(O)—R$_{11}$, —SO$_2$—R$_{11}$, —S(O)—CH$_2$—R$_{11}$, —SO$_2$—CH$_2$—R$_{11}$ or —NR$_{12}$R$_{13}$;
  R$_9$ representing —R$_{14}$, —NHR$_{14}$, —CH$_2$—NHR$_{14}$, —CH$_2$—NH—C(O)—R$_{14}$, —NH—CH$_2$—R$_{14}$, —NH—NH—R$_{14}$, —NH—C(O)—R$_{14}$, —NH—C(O)—CH$_2$—R$_{14}$, —NH—CH$_2$—C(O)—R$_{14}$, —NH—CH$_2$—C(O)—O—R$_{14}$, —NH—CH$_2$—C(O)—NH—R$_{14}$, —NH—SO$_2$—R$_{14}$, —S(O)—R$_{14}$, —SO$_2$—R$_{14}$, —S(O)—CH$_2$—R$_{14}$, —SO$_2$—CH$_2$—R$_{14}$ or —NR$_{16}$R$_{17}$;
  R$_{10}$ representing a —S(O)R$_{15}$ or —S(O)$_2$R$_{15}$ group;
  R$_{11}$ representing a hydrogen atom or a (C$_1$-C$_6$)alkyl, carbocycle, heterocycle, biaryl, carbocycle-(C$_1$-C$_6$)alkyl or heterocycle-(C$_1$-C$_6$)alkyl group, optionally substituted;
  R$_{12}$ and R$_{13}$ together forming, with their carrier nitrogen atom, a heterocycle optionally substituted with a —R$_{11}$, —OR$_{11}$ or —NHR$_{11}$ group;
  R$_{14}$ representing a (C$_1$-C$_6$)alkyl, carbocycle, heterocycle, biaryl, carbocycle-(C$_1$-C$_6$)alkyl or heterocycle-(C$_1$-C$_6$)alkyl group, optionally substituted;
  R$_{15}$ representing optionally substituted (C$_1$-C$_6$)alkyl group, optionally substituted aryl group, (C$_1$-C$_6$)alkyl-aryl, aryl-(C$_1$-C$_6$)alkyl, carbocycle, optionally substituted heterocycle, biaryl, carbocycle-(C$_1$-C$_6$)alkyl or heterocycle-(C$_1$-C$_6$)alkyl; and
  R$_{16}$ and R$_{17}$ together forming, with their carrier nitrogen atom, a heterocycle optionally substituted with a —R$_{14}$, —OR$_{14}$ or —NHR$_{14}$ group.

The absolute stereochemistry at the spiro ring junction and alpha carbon carrying a methyl group is such as indicated in formula (I) above. In addition, the

portion of the molecule of above-mentioned formula (I) may comprise one or more other asymmetric carbons which may each be present in the R or S configuration or else in the form of a mixture of the two configurations R and S in any proportion, in particular in equimolar proportions.

In the present invention by "pharmaceutically acceptable" is meant that which can be used to prepare a pharmaceutical composition which is generally safe, non-toxic and neither biologically nor otherwise adverse, and which is acceptable for veterinary use as well as for human pharmaceutical use.

By "pharmaceutically acceptable salts" of a compound in this invention it is meant to designate salts that are pharmaceutically acceptable as defined above and which have the desired pharmacological activity of the parent compound.

In particular these are acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like.

By "halogen atom" in the present invention is meant atoms of fluorine, chlorine, bromine and iodine.

By "$(C_1-C_6)$alkyl" in the present invention is meant a linear or branched, saturated hydrocarbon chain comprising 1 to 6 carbon atoms. In particular it may be a methyl, ethyl, n-propyl, isopropyl, n-butyl, iso-butyl, sec-butyl, tert-butyl, n-pentyl or n-hexyl group.

By "$(C_1-C_6)$alkoxy" in the present invention is meant a $(C_1-C_6)$alkyl group as defined above attached to the remainder of the molecule via an oxygen atom. It may in particular be a methoxy, ethoxy, n-propoxy, isopropoxy, n-butoxy, isobutoxy, sec-butoxy, tert-butoxy, n-pentoxy or n-hexoxy group.

By "aryl" in the present invention is meant an aromatic hydrocarbon group preferably having 5 to 10 carbon atoms and comprising one or more fused rings, preferably 1 or 2 rings, e.g. a phenyl or naphthyl group. Advantageously it is phenyl.

By "$(C_1-C_6)$alkyl-aryl" in the present invention is meant a $(C_1-C_6)$alkyl group as defined above attached to the remainder of the molecule via an aryl group as defined above. In particular it may be a tolyl group.

By "aryl-$(C_1-C_6)$alkyl" in the present invention is meant an aryl group as defined above attached to the remainder of the molecule via a $(C_1-C_6)$alkyl group as defined above. In particular, it may be a benzyl group.

By "biaryl" in the present invention is meant an aryl group as defined above attached to the remainder of the molecule via an aryl group as defined above. In particular it may be a biphenyl group.

By "heteroaryl" group in the present invention is meant an aryl group as defined above wherein one or more carbon atoms have been replaced by one or more heteroatoms, advantageously 1 to 4, preferably 1 or 2. Examples of heteroaryl groups are pyridine, pyrimidine, pyrazine, pyridazine, furan, thiophene, pyrrole, pyrazole, imidazole, thiazole, isothiazole, oxazole, isoxazole, triazole, tetrazole, benzofuran, benzothiophene, indole, benzimidazole, indazole, quinoline, isoquinoline, quinazoline or quinoxaline groups.

By "heteroatom" is particularly meant a sulfur, nitrogen or oxygen atom.

Par "carbocycle" in the present invention is meant one or more fused rings, preferably 1 or 2 saturated, unsaturated or aromatic hydrocarbon fused rings, each ring advantageously having 3 to 8 members, preferably 3, 5, 6 or 7 members, more preferably 5 or 6 members. It may in particular be a cycloalkyl such as a cyclopentyl or cyclohexyl.

By "unsaturated" in the present invention is meant that the ring comprises one or more double bonds.

By "carbocycle-$(C_1-C_6)$alkyl" in the present invention is meant a carbocycle group as defined above attached to the remainder of the molecule via a $(C_1-C_6)$alkyl group as defined above, preferably via a —$CH_2$— group. In particular, it may be a cyclopentyl-methyl or cyclohexyl-methyl group.

By "heterocycle" in the present invention is meant a carbocycle group as defined above wherein one or more carbon atoms have been replaced by one or more heteroatoms, advantageously 1 to 4, preferably 1 or 2. Examples of heterocycles comprising only 1 ring are the rings: epoxide, aziridine, furan, dihydrofuran, tetrahydrofuran, pyrrole, pyroline, pyrrolidine, thiophene, dihydrothiophene, tetrahydrothiophene, pyrazole, pyrazoline, pyrazolidine, imidazole, imidazoline, imizadolidine, thiazole, dihydrothiazole, tetrahydrothiazole, oxazole, dihydrooxazole, tetrahydrooxazole, triazoles, dihydrotriazoles, tetrahydrotriazoles, pyridine, dihydropyridine, tetrahydropyridine, piperidine, pyrimidine, pyridazine, pyrazine, dihydropyrimidine, dihydropyridazine, dihydropyrazine, tetrahydropyrimidine, tetrahydropyridazine, tetrahydropyrazine, hexahydropyrimidine, hexahydropyridazine, piperazine, pyran, dihydropyran, tetrahydropyran, oxazines, dihydrooxazines, tetrahydrooxazines (e.g. morpholine), azepine, dihydroazepine, tetrahydroazepine, azepane, diazepines, dihydrodiazepines, tetrahydrodiazepines and diazepanes. Examples of heterocycles comprising 2 fused rings are the previously mentioned 1-ring heterocycles fused with 1 phenyl core such as indole, benzofuran, benzopyran including chromene and isochromene, dihydrobenzopyrans including chromane, quinoline, dihydroquinolines, tetrahydroquinoline, isoquinoline, dihydroisoquinolines and tetrahydroisoquinoline.

By "heterocycle-$(C_1-C_6)$alkyl" in the present invention is meant a heterocycle group as defined above attached to the remainder of the molecule via a $(C_1-C_6)$alkyl group as defined above, and preferably via a —$CH_2$— group.

By "cycloalkyl" in the present invention is meant a saturated, hydrocarbon, monocycle advantageously comprising 3 to 8 carbon atoms, in particular 5 or 6. In particular, it may be a cyclohexyl.

According to one particular embodiment of the invention:
$R_1$ to $R_5$ are each independently a hydrogen atom or a $(C_1-C_6)$alkyl, aryl, $(C_1-C_6)$alkyl-aryl or aryl-$(C_1-C_6)$alkyl group;
$R_6$ is a hydrogen atom or a $(C_1-C_6)$alkyl, aryl, $(C_1-C_6)$alkyl-aryl, aryl-$(C_1-C_6)$alkyl, $C(O)NH_2$ or $C(S)NH_2$ group; and
$R_7$ is a $(C_1-C_6)$alkyl, aryl, $(C_1-C_6)$alkyl-aryl or aryl-$(C_1-C_6)$alkyl group.

According to the invention, Y is C=O, C=S, $CH_2$, CH—$OR_1$, $CHN_3$, $CHNR_2R_3$, C=N—$OR_4$ or C=N—$NR_5R_6$, for example C=O, CH—$OR_1$, $CHN_3$, $CHNR_2R_3$, C=N—$OR_4$ or C=N—$NR_5R_6$, and advantageously C=O, CH—$OR_1$, C=N—$OR_4$, or C=N—$NR_5R_6$ group, in particular C=O or CH—$OR_1$ such as C=O or CH—OH, and particularly C=O.

---- advantageously represents a double bond.

In a first embodiment, Z is a-$S(O)R_7$ or —$S(O)_2R_7$ group, and X is a CH—$R_8$ group when ---- represents a single bond, or C—$R_8$ when ---- represents a double bond, preferably X represents C—$R_8$.

$R_7$ is a $(C_1-C_6)$alkyl, aryl, $(C_1-C_6)$alkyl-aryl or aryl-$(C_1-C_6)$alkyl group, preferably an aryl or $(C_1-C_6)$alkyl-aryl group.

$R_8$ advantageously represents a $R_{11}$ group.

$R_{11}$ is advantageously a hydrogen atom or a $(C_1-C_6)$alkyl, carbocycle, heterocycle, biaryl, carbocycle-$(C_1-C_6)$alkyl or heterocycle-$(C_1-C_6)$alkyl group, optionally substituted; in particular a hydrogen atom or a ($C_1$-$C_6$)alkyl, carbocycle, heterocycle or biaryl group, optionally substituted; preferably a hydrogen atom or a ($C_1$-$C_6$)alkyl group such as a $CH_3$ group; for example a hydrogen atom, the carbocycle advantageously being a cycloalkyl such as a cyclohexyl or an aryl such as phenyl or naphthyl, the heterocycle advantageously being pyridine, pyrimidine, pyridazine, pyrazine, furan, thiophene, pyrrole, pyrazole, imidazole, thiazole, oxazole, triazoles, benzofuran, benzothiophene, indole, 1,3-benzodioxolane, piperidine, morpholine or piperazine; particularly pyridine, furan, thiophene, pyrrole, benzofuran, benzothiophene, indole, 1,3-benzodioxolane or piperidine and more particularly pyridine, furan, thiophene, benzofuran, 1,3-benzodioxolane or piperidine, and the biaryl advantageously being biphenyl.

When the ($C_1$-$C_6$)alkyl, carbocycle, heterocycle, biaryl, carbocycle-($C_1$-$C_6$)alkyl or heterocycle-($C_1$-$C_6$)alkyl group of $R_{11}$ is substituted, it is advantageously substituted with a halogen atom; an oxo group (=O); CN; $CO_2H$; $CO_2$—($C_1$-$C_6$)alkyl; OH; $NR_{18}R_{19}$; an aryl optionally substituted with one or more substituents selected from among a halogen atom, ($C_1$-$C_6$)alkyl, OH or ($C_1$-$C_6$)alkoxy; a heterocycle; or a ($C_1$-$C_6$)alkyl or ($C_1$-$C_6$)alkoxy group optionally substituted with one or more substituents selected from among a halogen atom, a ($C_1$-$C_6$)alkoxy group, a heterocycle or $NR_{20}R_{21}$, the groups $R_{18}$ to $R_{21}$ each independently representing a hydrogen atom or a ($C_1$-$C_6$)alkyl or aryl group, and the heterocycles optionally being substituted with an oxo, ($C_1$-$C_6$)alkyl or $CO_2$—($C_1$-$C_6$)alkyl group.

In a second embodiment, Z is a hydrogen atom or a $R_9$ group, and X is a CH—$R_{10}$ group when ---- represents a single bond, or C—$R_{10}$ when ---- represents a double bond, preferably X represents a C—$R_{10}$ group.

Z is preferably a hydrogen atom.

When Z represents a —$R_9$ group, $R_9$ preferably represents a $R_{14}$ group, $R_{14}$ then preferably representing a hydrogen atom or a ($C_1$-$C_6$)alkyl, carbocycle, heterocycle, biaryl, carbocycle-($C_1$-$C_6$)alkyl or heterocycle-($C_1$-$C_6$)alkyl group, optionally substituted; in particular a ($C_1$-$C_6$)alkyl, carbocycle, heterocycle or biaryl group, optionally substituted; preferably a ($C_1$-$C_6$)alkyl group such as a $CH_3$ group, the carbocycle advantageously being a cycloalkyl such as cyclohexyl or an aryl such as phenyl or naphthyl, the heterocycle advantageously being pyridine, pyrimidine, pyridazine, pyrazine, furan, thiophene, pyrrole, pyrazole, imidazole, thiazole, oxazole, triazoles, benzofuran, benzothiophene, indole, 1,3-benzodioxolane, piperidine, morpholine or piperazine; particularly pyridine, furan, thiophene, pyrrole, benzofuran, benzothiophene, indole, 1,3-benzodioxolane or piperidine; more particularly pyridine, furan, thiophene, benzofuran, 1,3-benzodioxolane or piperidine, and the biaryl advantageously being the biphenyl.

When the ($C_1$-$C_6$)alkyl, carbocycle, heterocycle, biaryl, carbocycle-($C_1$-$C_6$)alkyl or heterocycle-($C_1$-$C_6$)alkyl group of $R_{11}$ is substituted, it is advantageously substituted with a halogen atom; an oxo group (=O); CN; $CO_2H$; $CO_2$—($C_1$-$C_6$)alkyl; OH; $NR_{22}R_{23}$; an aryl optionally substituted with one or more substituents selected from among a halogen atom, ($C_1$-$C_6$)alkyl, OH or ($C_1$-$C_6$)alkoxy; a heterocycle; or a ($C_1$-$C_6$)alkyl or ($C_1$-$C_6$)alkoxy group optionally substituted with one or more substituents selected from among a halogen atom, a ($C_1$-$C_6$)alkoxy group, a heterocycle or $NR_{24}R_{25}$, the groups $R_{22}$ to $R_{25}$ each independently representing a hydrogen atom or a ($C_1$-$C_6$)alkyl or aryl group, and the heterocycles optionally being substituted with an oxo, ($C_1$-$C_6$)alkyl or $CO_2$—($C_1$-$C_6$)alkyl group.

$R_{10}$ preferably represents a —$S(O)_2R_{15}$ group.

$R_{15}$ represents optionally substituted ($C_1$-$C_6$)alkyl, optionally substituted aryl, ($C_1$-$C_6$)alkyl-aryl, aryl-($C_1$-$C_6$)alkyl, carbocycle, optionally substituted heterocycle, biaryl, carbocycle-($C_1$-$C_6$)alkyl or heterocycle-($C_1$-$C_6$)alkyl.

When the ($C_1$-$C_6$)alkyl, aryl or heterocycle group of $R_5$ is substituted, it is advantageously substituted with one or more substituents selected from among a halogen atom; an oxo group (=O) [except for the aryl group]; $CO_2R_{26}$; $OR_{27}$; $NR_{28}R_{29}$; ($C_1$-$C_6$)alkyl group; and an aryl optionally substituted with one or more substituents selected from among a halogen atom, ($C_1$-$C_6$)alkyl, OH or ($C_1$-$C_6$)alkoxy, particularly selected from among a halogen atom: oxo group (=O) [except for the aryl group]; $CO_2R_{26}$; $OR_{27}$; $NR_{28}R_{29}$; ($C_1$-$C_6$)alkyl;

selected in particular from among $CO_2R_{26}$, $OR_{27}$ and $NR_{28}R_{29}$, more particularly from among $OR_{27}$ and $NR_{28}R_{29}$, the groups $R_{26}$ to $R_{29}$ each independently representing a hydrogen atom or ($C_1$-$C_6$)alkyl or aryl group.

$R_{15}$ is preferably a ($C_1$-$C_6$)alkyl group optionally substituted with one or more groups (in particular one group) selected from among $CO_2R_{26}$, $OR_{27}$ and $NR_{28}R_{29}$, more particularly from among $OR_{27}$ and $NR_{28}R_{29}$; aryl; ($C_1$-$C_6$)alkyl-aryl; or aryl-($C_1$-$C_6$)alkyl.

In particular, the compounds of the invention can be selected from among the following examples:

| Compound N° | Structures |
|---|---|
| 95 | 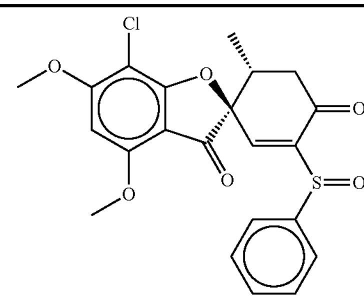 |
| 96 | 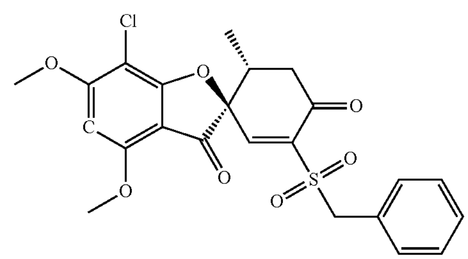 [SMILES: COc1cc(OC)c2c(c1Cl)O[C@@]1(C=C(S(=O)(=O)Cc3ccccc3)C(=O)C[C@H]1C)C2=O] |
| 97 | 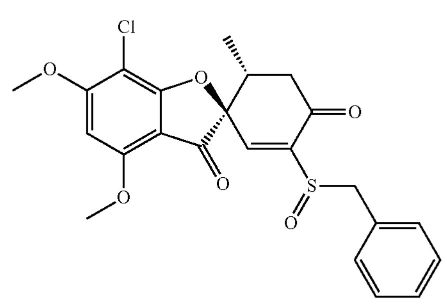 [SMILES: COc1cc(OC)c2c(c1Cl)O[C@@]1(C=C(S(=O)Cc3ccccc3)C(=O)C[C@H]1C)C2=O] |

-continued

| Compound N° | Structures |
|---|---|
| 98 | 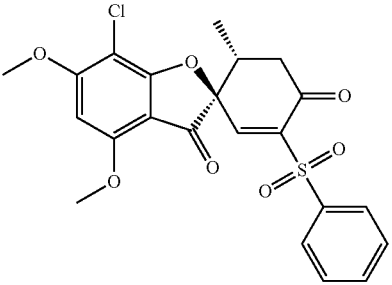 [SMILES: COc1cc(OC)c2c(c1Cl)O[C@@]1(C=C(S(=O)(=O)c3ccccc3)C(=O)C[C@H]1C)C2=O] |
| 145 | 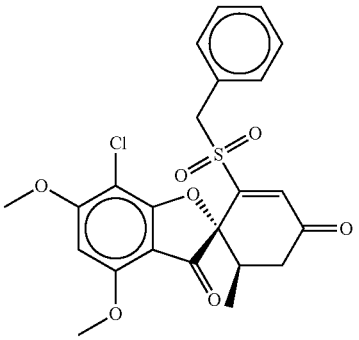 |
| 146 | 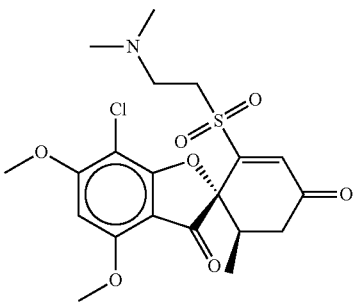 |
| 147 | 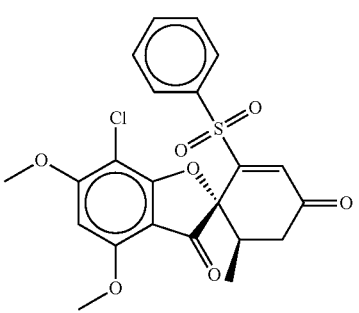 |
| 148 | 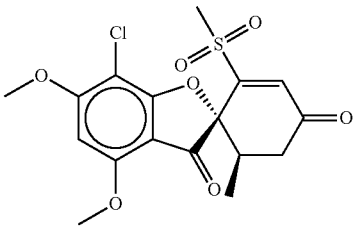 |

A further subject of the invention is a formula (I) compound of the invention such as defined above, for use as a drug, notably intended for the treatment of cancerous and pre-cancerous hyperproliferative pathologies.

The present invention also concerns the use of a formula (I) compound such as defined above in the manufacture of a drug, notably intended for the treatment of cancerous and pre-cancerous hyperproliferative pathologies.

The present invention also concerns a method for treating cancerous and pre-cancerous hyperproliferative pathologies, comprising the administration of an efficient dose of a formula (I) compound as defined above to a person in need thereof.

By "cancerous or pre-cancerous hyperproliferative pathologies" in the present invention is meant all types of cancerous or pre-cancerous hyperproliferative pathologies, in particular lung cancer, breast cancer, brain cancer and skin cancers.

By "skin cancer" in the present invention is meant actinic keratosis, solar keratosis, keratinocyte intraepithelial neoplasia, cutaneous papilloma, in situ epidermoid carcinoma, epidermoid carcinoma, pre-cancerous skin lesions, basal cell carcinoma including surface and nodular forms, Bowen's disease, Dubreuilh's melanoma, condylomas, Merkel cell tumour, Paget's disease, or cutaneous-mucosal lesions caused by human papilloma virus.

The present invention also concerns a pharmaceutical composition comprising at least one formula (I) compound as defined above, and at least one pharmaceutically acceptable excipient.

The pharmaceutical compositions of the invention can be formulated in particular for oral administration, for administration via topical route or via injection, the said compositions being more particularly intended for mammals including human.

The active ingredient can be administered in unit administration forms, in a mixture with conventional pharmaceutical carriers, to animals including human beings. The compounds of the invention as active ingredients can be used at doses of between 0.01 mg and 1000 mg per day, given in a single dose once daily or administered in several doses throughout the day, for example twice a day in equal doses. The dose administered per day is advantageously between 5 mg and 500 mg, more advantageously between 10 mg and 200 mg. It may be necessary to use doses outside these ranges as can be determined by persons skilled in the art.

The pharmaceutical compositions of the invention may also comprise at least one other active ingredient such as an anti-cancer agent.

The present invention further concerns a pharmaceutical composition such as defined above for use as a drug, notably intended for the treatment of cancerous and pre-cancerous hyperproliferative pathologies The present invention is illustrated by the following non-limiting examples.

EXAMPLE 1

Synthesis of the Compounds of the Invention

Abbreviations Used

DMF Dimethylformamide
DMSO Dimethylsulfoxide
equiv./eq., Eq.uivalent
PE Petroleum ether
ES Electrospray ionization
HPLC High Performance Liquid Chromatography LCMS Liquid chromatography coupled with mass spectrometry
NMR Nuclear Magnetic Resonance
rt Room temperature
THF Tetrahydrofuran The compounds of the invention were often obtained in the form of two diastereoisomers which were able to be separated. However, among the two NMR spectra obtained it was not determined to which spectrum each of these two diastereoisomers corresponded.

1.1. Synthesis of a Sulfoxide at 3'

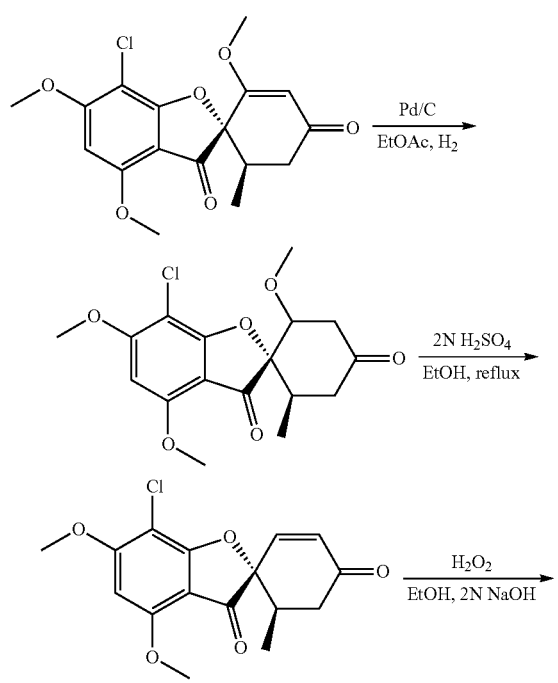

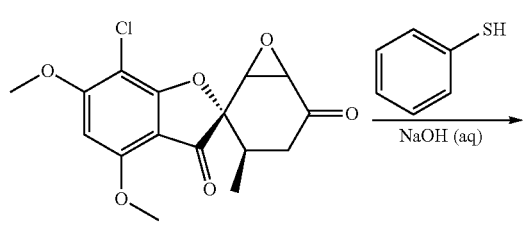

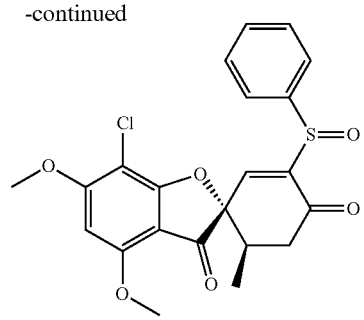

A 2 L round-bottomed flask was charged with 3 g of Pd/C in a solution of griseofulvin (20 g, 5.7 mmol) in 1.2 L of AcOEt. The mixture was left under agitation in a hydrogen atmosphere (1 bar) at ambient temperature for 60 h, then filtered. The filtrate was concentrated under reduced pressure. A white solid was obtained (20 g) and used as crude product at the following step.

(2S,6'R)-7-chloro-4,6-dimethoxy-6'-methyl-3H-spiro[benzofuran-2,1'-cyclohexan]-2'-ene-3,4'-dione In a 2 L round-bottomed flask 600 mL of 2N sulfuric acid was added dropwise to a solution of the product previously obtained (60 g, 169.1 mmol) in 600 mL of ethanol. The resulting solution was heated under reflux for 16 h, then cooled to ambient temperature. The reaction medium was extracted with 2×400 mL of dichloromethane. The organic phases were combined, dried over anhydrous sodium sulfate and concentrated under reduced pressure. A pale yellow solid (54 g) was obtained with a yield of 99%.

$^1$H NMR (CDCl$_3$, 400 MHz, δ, ppm): 6.57 (1H, d), 6.19 (1H, d), 6.15 (1H, s), 4.04 (3H, s), 4.00 (3H, s), 3.12 (1H, dd), 2.94-2.81 (1H, m), 2.42 (1H, dd), 0.97 (3H, d)

LCMS (ES, m/z): 322.90 [M+H]$^+$ (2S,3'R)-7-chloro-4,6-dimethoxy-3'-methyl-3H-7'-oxaspiro[benzofuran-2,2'-bicyclo[4.1.0]heptane]-3,5'-dione In a 100 ml, round-bottomed flask a 2N solution of NaOH was added dropwise to a solution of 0.5 g (1.55 mmol, 1 equiv.) of the product previously obtained in 20 mL of ethanol under agitation at 0° C. H$_2$O$_2$ (1 mL) was added dropwise to the agitated solution at 0° C. The reaction mixture was left under agitation 1 h at 0° C. then diluted in 100 mL of water. The solution was extracted with 3×100 mL of AcOEt. The organic phases were combined, dried over anhydrous sodium sulfate and filtered. The filtrate was concentrated under reduced pressure. A pale yellow solid (m=0.5 g) was obtained with a yield of 95%.

$^1$H NMR (DMSO-d6, 400 MHz, δ, ppm): 6.52 (1H, s), 4.05 (3H, s), 4.05-4.00 (1H, m), 3.94 (3H, s), 3.58-3.56 (1H, m), 2.80-2.68 (1H, m), 2.65-2.55 (1H, m), 2.31-2.21 (11H, m), 0.63 (3H, d)

LCMS (ES, m/z): 338.85 [M+H]$^+$

In a 100 mL round-bottomed flask 4 mL of 0.1 N NaOH was added to a solution of thiophenol (176 mg, 1.6 mmol, 1.2 eq.) in 20 mL of water. The mixture was agitated 10 min at 30° C. The previously obtained product (0.45 g, 1.3 mmol, 1.0 eq.) was added and the mixture left under agitation 1 h at 30° C., then 16 h at 70° C. The reaction mixture was cooled to ambient temperature then extracted with 3×30 mL AcOEt. The organic phases were combined, dried over anhydrous sodium sulfate, filtered and concentrated under reduced pressure. The residue was purified by chromatography on silica gel (AcOEt/EP 1:2). A pale yellow solid (360 mg) was obtained with a yield of 63%.

1'S,6'R)-7-chloro-4,6-dimethoxy-6'-methyl-3'-(phenylsulfinyl)-3H-spiro[benzofuran-2,1'-cyclohex[2]ene]-3,4'-dione 95 In a 100 mL round-bottomed flask, to a solution of the product previously obtained (0.35 g, 0.8 mmol, 1.0 eq.) in 20 mL methanol was added 261 mg (1.2 mmol, 1.5 eq.) of sodium periodate dissolved in 10 mL of water. The solution was left under agitation at 50° C. for 16 h. The reaction mixture was cooled to ambient temperature and extracted with 3×50 mL of dichloromethane. The organic phases were combined, dried over anhydrous sodium sulfate, filtered and concentrated under reduced pressure. The residue was purified by chromatography on silica gel (EtOAc/EP 1:2). A white solid (0.2 g) was obtained with a yield of 55%.

$^1$H NMR (300 MHz, CD$_3$OD, δ, ppm): 7.78-7.84 (1H, m), 7.70-7.73 (1H, dd, J=6 Hz), 7.51-7.58 (3H, m), 7.28-7.30 (1H, d, J=5.4 Hz), 6.48 (1H, s), 4.85 (3H, s), 4.09 (3H, s), 2.73-3.07 (2H, m), 2.41-2.54 (1H, m), 0.86-0.90 (3H, t, J=6.6 Hz); LCMS (ES, m/z): 447 [M+H]$^+$ The following sulfoxides were prepared following similar procedure.

(1'S,6'R)-3'-(benzylsulfonyl)-7-chloro-4,6-dimethoxy-6'-methyl-3H-spiro[benzofuran-2,1'-cyclohex[2]ene]-3,4'-dione 96 White solid 79% yield; $^1$H (CDCl$_3$, 400 MHz, δ, ppm): 0.93 (d, 3H, J=6.7 Hz), 2.63 (dd, 1H, J=17.6, 5.3 Hz), 2.80 (m, 1H), 3.21 (dd, 1H, J=17.6, 13.7 Hz), 3.98 (s, 3H), 4.03 (s, 3H), 4.56 (d, 1H, J=13.7 Hz), 4.63 (d, 1H, J=13.7 Hz), 6.14 (s, 1H), 7.27-7.34 (m, 5H); LCMS (ES, m/z): 477.1 [M+H]$^+$

(1'S,6'R)-3'-(benzylsulfinyl)-7-chloro-4,6-dimethoxy-6'-methyl-3H-spiro[benzofuran-2,1'-cyclohex[2]ene]-3,4'-dione 97 White solid 30% yield; $^1$H (CDCl$_3$, 400 MHz, δ, ppm): 0.97 (d, 3H, J=6.7 Hz), 2.60 (dd, 1H, J=17.3, 5.0 Hz), 2.88-2.96 (m, 1H), 3.27 (dd, 1H, J=17.4, 13.8 Hz), 3.90 (d, 1H, J=13.0 Hz), 4.01 (s, 3H), 4.03 (s, 3H), 4.35 (d, 1H, J=13.0 Hz), 6.14 (s, 1H), 6.87 (s, 1H), 7.20 (d, 2H, J=7.7 Hz), 7.26-7.34 (m, 3H); LCMS (ES, m/z): 461.1 [M+H]$^+$

(1'S,6'R)-7-chloro-4,6-dimethoxy-6'-methyl-3'-(phenylsulfonyl)-3H-spiro[benzofuran-2,1'-cyclohex[2]ene]-3,4'-dione 98 White solid 46% yield; $^1$H (CDCl$_3$, 400 MHz, δ, ppm): 0.92 (d, 3H, J=6.7 Hz), 2.46 (dd, 1H, J=17.2, 4.9 Hz), 2.86-2.94 (m, 1H), 3.13 (dd, 1H, J=17.2, 14.0 Hz), 4.00 (s, 3H), 4.06 (s, 3H), 6.18 (s, 1H), 7.52 (t, 2H, J=7.4 Hz), 7.62 (t, 1H, J=7.4 Hz), 7.78 (s, 1H), 8.01 (d, 2H, J=7.4 Hz); LCMS (ES, m/z): 463.0 [M+H]$^+$

1.2. Forming of Sulfones at 2'

Method A:

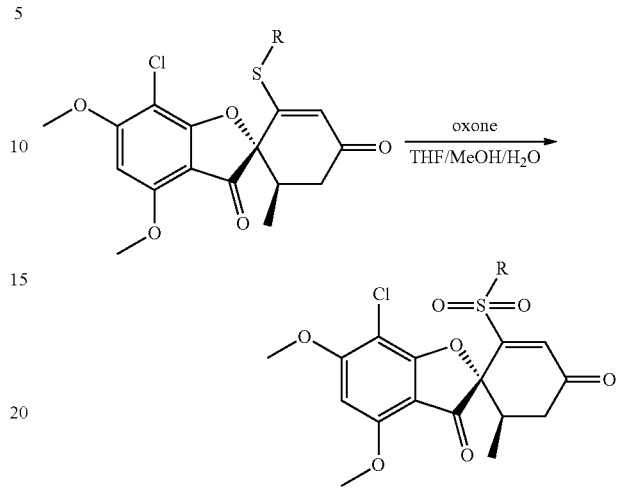

EXAMPLE

R=Bn

Synthesis of the Sulfide:

In a 100 mL round-bottomed flask, thiol (RSH) (5.6 mmol, 2 eq.) was added to a 1 g solution of (1'R,6'R)-2',7-dichloro-4,6-dimethoxy-6'-methyl-3H-spiro[benzofuran-2,1'-cyclohex[2]ene]-3,4'-dione (1 g, 2.8 mmol, 1 eq.) and 1.05 mL of 1,8-diazabicyclo[5.4.0]undec-7-ene (7.0 mmol, 2.5 eq.) dissolved in 10 mL of 1,4-dioxane. The mixture was brought to 100° C. for 16 h. The reaction mixture was then cooled to ambient temperature and diluted in water and dichloromethane. The organic phase was washed with saturated NaHCO$_3$ solution, dried over MgSO$_4$, filtered and concentrated under reduced pressure. The residue was purified by chromatography on silica gel (eluting with dichloromethane/methanol).

Synthesis of the Sulfone:

In a 250 ml round-bottomed flask, 4.6 g of oxone monopersulfate (13.0 mmol) dissolved in 46 ml of water was added to a solution of the sulfide (768 mg, 1.7 mmol) in 15 mL of methanol (15 mL) and 15 mL of THF. The reaction mixture was left under agitation at ambient temperature for 16 h. The solids were filtered and rinsed with methanol. The filtrate was concentrated under reduced pressure then diluted in AcOEt and water. The aqueous phase was extracted with AcOEt. The organic phases were combined, dried over MgSO$_4$, filtered and concentrated under reduced pressure. The residue was purified by chromatography on silica gel (CH$_2$Cl$_2$/AcOEt 98:2). A beige solid (0.26 g) was obtained with a yield of 32%.

Method B:

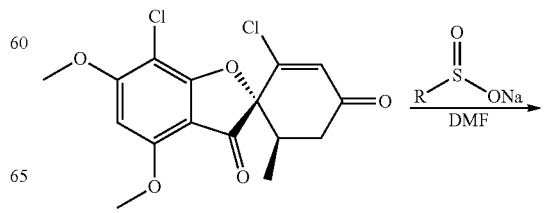

-continued

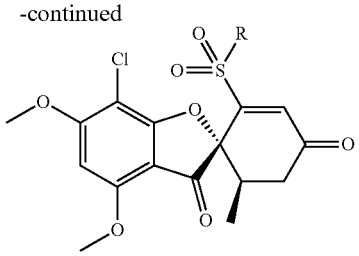

Example R=Ph (147)

In a 50 mL round-bottomed flask, 46 mg (0.28 mmol, 1 eq.) of sodium benzenesulfinate was added to a solution of 100 mg of (1'R,6'R)-2',7-dichloro-4,6-dimethoxy-6'-methyl-3H-spiro[benzofuran-2,1'-cyclohex[2]ene]-3,4'-dione (0.28 mmol, 1 eq.) in 1 mL of DMF. The mixture was left under agitation at ambient temperature for 16 h. Water was added to the reaction medium and the precipitate obtained was filtered, rinsed with water and dried under reduced pressure. A white solid was obtained with a yield of 86%.

(1'R,6'R)-2'-(benzylsulfonyl)-7-chloro-4,6-dimethoxy-6'-methyl-3H-spiro[benzofuran-2,1'-cyclohex[2]ene]-3,4'-dione 145 $^1$H NMR (CDCl$_3$, 400 MHz, δ, ppm): 0.96 (d, 3H, J=6.8 Hz), 2.39 (dd, 1H, J=17.6, 4.8 Hz), 2.74 (m, 1H), 3.07 (dd, 1H, J=17.6, 14.0 Hz), 3.99 (s, 3H), 4.06 (s, 3H), 4.49 (d, 1H, J=13.6 Hz), 4.69 (d, 1H, J=13.6 Hz), 6.19 (s, 1H), 6.52 (s, 1H), 7.37 (m, 3H), 7.49 (m, 2H); LCMS (ES, m/z): 477.07 [M+H]$^+$ (1'R,6'R)-7-chloro-2'-(2-(dimethylamino)ethylsulfonyl)-4,6-dimethoxy-6'-methyl-3H-spiro[benzofuran-2,1'-cyclohex[2]ene]-3,4'-dione 146 pale yellow solid, yield 11%; $^1$H NMR (CDCl$_3$, 400 MHz, δ, ppm): 0.95 (d, 3H, J=6.8 Hz), 2.27 (s, 6H), 2.50 (dd, 1H, J=17.6, 4.8 Hz), 2.66 (dt, 1H, J=13.2, 5.2 Hz), 2.87 (m, 2H), 3.18 (m, 2H), 3.77 (ddd, 1H, J=14.4, 8.8, 6.0 Hz), 3.98 (s, 3H), 4.03 (s, 3H), 6.16 (s, 1H), 6.88 (s, 1H); LCMS (ES, m/z): 458.096 [M+H]$^+$ (1'R,6'R)-7-chloro-4,6-dimethoxy-6'-methyl-2'-(phenylsulfonyl)-3H-spiro[benzofuran-2,1'-cyclohex[2]ene]-3,4'-dione 147 pale yellow solid, yield 13%; $^1$H NMR (CDCl$_3$, 400 MHz, δ, ppm): 0.83 (d, 1H, J=6.8 Hz), 2.44 (dd, 1H, J=17.2, 4.8 Hz), 2.77 (m, 1H), 3.11 (dd, 1H, J=17.2, 14.0 Hz), 4.00 (s, 3H), 4.05 (s, 3H), 6.18 (s, 1H), 7.11 (s, 1H), 7.54 (t, 2H, J=7.6 Hz), 7.65 (t, 1H, J=7.6 Hz), 7.83 (d, 2H, J=7.2 Hz); LCMS (ES, m/z): 463.054 [M+H]$^+$ (1'R,6'R)-7-chloro-4,6-dimethoxy-6'-methyl-2'-(methylsulfonyl)-3H-spiro[benzofuran-2,1'-cyclohex[2]ene]-3,4'-dione 148 pale yellow solid, yield 12%; $^1$H NMR (CDCl$_3$, 400 MHz, δ, ppm): 0.97 (d, 3H, J=6.8 Hz), 2.52 (dd, 1H, J=17.2, 4.4 Hz), 2.94 (m, 1H), 3.17 (dd, 1H, J=17.2, 14.0 Hz), 3.22 (s, 3H), 3.98 (s, 3H), 4.03 (s, 3H), 6.16 (s, 1H), 6.98 (s, 1H); LCMS (ES, m/z): 401.038 [M+H]$^+$

EXAMPLE 2

Cytotoxic Activity of the Compounds of the Invention

Culture of Lines and Measurement of Cell Viability:

The lines NIE115 (ATCC, CRL2263), MDA-MB-231 (ATCC, HTB26) and HSC-1 (Health Science Research Resources Bank, JCRB1015) were cultured in DMEM medium (Dulbecco's modified Eagle medium) supplemented with 2 mM of L-Glutamine (Sigma, G7513) and 10% foetal calf serum (Hyclone, SH30109.03) or 20% for the HSC-1 cells. The HCC-1937 (ATCC, CRL2336) and A549 (ATCC, CCL185) lines were cultured in RPMI medium (Roswell Park Memorial Institute medium) supplemented with 10% foetal calf serum and 2 mM of L-Glutamine. Finally, the SCC114 line (DSMZ, ACC662) was cultured in MEM medium (Minimum Essential Medium Eagle) supplemented with 10% foetal calf serum and 2 mM of L-Glutamine. Initially, in 96-well plates (Perkin Elmer, 6005668), the cells were seeded in their respective culture media with 750 cells per well for NIE115; 1000 cells per well for SCC114 and A549; 2000 cells per well for HCC-1937 and HSC-1; 2500 cells per well for MDA-MB-231. Cascade dilution of each compound was performed in dimethylsulfoxide (DMSO) (Sigma, D8418) using 10 mM stock solutions in 100% DMSO. Each of the dilutions was added to the cells 24 hours after seeding. Under these conditions the final solvent concentration was 0.1% DMSO. Reading of cell proliferation was conducted 72 hours after addition of products with the ATPLite kit (Perkin Elmer, 6016947) and following the manufacturer's directions except in the case of the HCC-1937 line for which this reading was carried out 48 hours after treatment. Analysis of proliferation results was performed by comparing with conditions in which solely the vehicle was added to the cells. The dose-response curves obtained were analysed using Prism 4.03 software (GraphPad Software Inc.) to determine the concentration of each compound allowing 50% inhibition of cell proliferation (IC$_{50}$). As examples, the cytotoxic properties of some compounds of the invention evaluated on the lines A549 (lung cancer cell line), MDA-MB-231 (mammary adenocarcinoma cell line), NIE115 (mouse brain neuroblastoma cell line), HCC-1937 1 (primary ductal breast carcinoma cell line), HSC-1 (cutaneous squamous carcinoma cell line) and SCC114 (oral squamous carcinoma cell line) are reported in Table 1, as compared with griseofulvin used as control product. The concentration values are expressed in micromolar units (µM).

TABLE 1

| | IC$_{50}$ (µM) | | | | | |
|---|---|---|---|---|---|---|
| Compound | N1E-115 | MDA-MB-231 | SCC114 | HCC1937 | HSC-1 | A549 |
| Griseofulvin | >10 | >10 | 6.4 | >10 | >10 | >10 |
| GF-15* | 1.1 | 1 | 0.98 | >10 | 4.3 | 2.9 |
| 95 | 1 | 0.54 | 0.25 | 0.43 | 0.32 | 0.25 |
| 96 | | | | 0.92 | | |
| 97 | | | 0.021 | | 0.14 | |
| 98 | | | 0.41 | 0.7 | 0.76 | |
| 145 | 3 | 2 | 0.385 | 1.4 | 1.4 | 1.5 |
| 146 | | | | 5.9 | | |
| 147 | | | | 1.6 | | |

*compound 15 of J. Med. Chem. 2009, 3342-3347

The activity of the compounds of the invention on the HCC1997 line was compared with that of known cytotoxics (Epotilone B and Vinflunine). The compounds of the invention exhibit particularly remarkable activity on this particularly resistant breast cancer cell line.

Additionally, comparative examples were performed between the compounds of the invention and compounds substituted at 2' with an $SR_7$ group. It is shown herein that substitution by a —$S(O)R_7$ or —$SO_2R_7$ group significantly improves the cytotoxic activity of the compounds compared with substitution with a-$SR_7$ group (compound 145 versus A and compound 146 versus B).

All these results are given in following Table 2.

TABLE 2

| Compound | Structure | $IC_{50}$ (μM) HCC1937 |
|---|---|---|
| 95 | 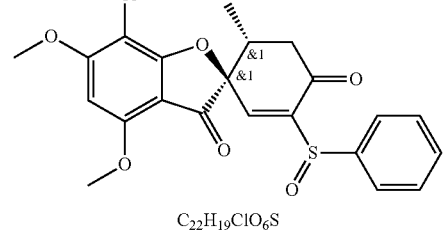 $C_{22}H_{19}ClO_6S$ | 0.43 |
| 98 | 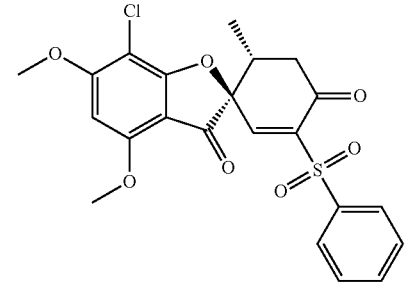 $C_{22}H_{19}ClO_7S$ | 0.7 |
| 96 | 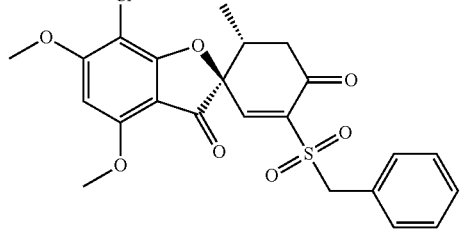 $C_{23}H_{21}ClO_7S$ | 0.92 |
| 147 | 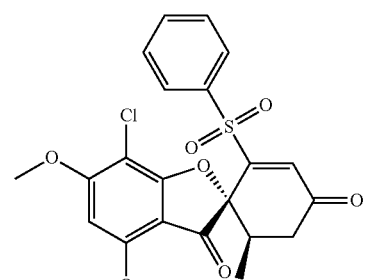 $C_{22}H_{19}ClO_7S$ | 1.6 |

TABLE 2-continued

| Compound | Structure | IC$_{50}$ (μM) HCC1937 |
|---|---|---|
| 145 | C$_{23}$H$_{21}$ClO$_7$S | 1.4 |
| A | C$_{23}$H$_{21}$ClO$_5$S | >10 |
| B | C$_{20}$H$_{24}$ClNO$_5$S | >10 |
| 146 | C$_{20}$H$_{24}$ClNO$_7$S | 5.9 |

TABLE 2-continued

| Compound | Structure | IC$_{50}$ (μM) HCC1937 |
|---|---|---|
| Epotilone B | C$_{27}$H$_{41}$NO$_6$S | >10 |
| Vinflunine | C$_{45}$H$_{54}$F$_2$N$_4$O$_8$ | >10 |

The invention claimed is:

1. A compound of following formula (I):

(I)

or a pharmaceutically acceptable salt thereof,
where:
===== represents a single or double bond;
—Y is C═O, C═S, CH—OR$_1$, CHN$_3$, CHNR$_2$R$_3$, C═N—OR$_4$, C═N—NR$_5$R$_6$,
Z is a —S(O)R$_7$ or —S(O)$_2$R$_7$ group,
and X is a CH—R$_8$ group when ===== represents a single bond, or C—R$_8$ when ===== represents a double bond;
with:
R$_1$ to R$_5$ each independently representing a hydrogen atom or a (C$_1$-C$_6$)alkyl, aryl, (C$_1$-C$_6$)alkyl-aryl, aryl-(C$_1$-C$_6$)alkyl or 5- or 6-membered heterocycle group;
R$_6$ representing a hydrogen atom or a (C$_1$-C$_6$)alkyl, aryl, (C$_1$-C$_6$)alkyl-aryl, aryl-(C$_1$-C$_6$)alkyl, C(O)NH$_2$, C(S)NH$_2$ or 5- or 6-membered heterocycle group;
R$_7$ representing a (C$_1$-C$_6$)alkyl, aryl, (C$_1$-C$_6$)alkyl-aryl, aryl-(C$_1$-C$_6$)alkyl or 5- or 6-membered heterocycle group;
R$_8$ representing —R$_{11}$, —NHR$_{11}$, —CH$_2$—NHR$_{11}$, —CH$_2$—NH—C(O)—R$_{11}$, —NH—CH$_2$—R$_{11}$, —NH—NH—R$_{11}$, —NH—C(O)—R$_{11}$, —NH—C(O)—CH$_2$—R$_{11}$, —NH—CH$_2$—C(O)—R$_{11}$, —NH—CH$_2$—C(O)—O—R$_{11}$, —NH—CH$_2$—C(O)—NH—R$_{11}$, —NH—SO$_2$—R$_{11}$, —S(O)—R$_{11}$, —SO$_2$—R$_{11}$, —S(O)—CH$_2$—R$_{11}$, —SO$_2$—CH$_2$—R$_{11}$ or —NR$_{12}$R$_{13}$;
R$_{11}$ representing a hydrogen atom or a (C$_1$-C$_6$)alkyl, carbocycle, heterocycle, biaryl, carbocycle-(C$_1$-C$_6$)alkyl or heterocycle-(C$_1$-C$_6$)alkyl group, optionally substituted; and
R$_{12}$ and R$_{13}$ together forming, with their nitrogen atom carrier, a heterocycle optionally substituted with —R$_{11}$, —OR$_{11}$ or —NHR$_{11}$.

2. The compound according to claim 1, wherein Y is a C═O or CH—OR$_1$ group.

3. The compound according to claim 1, wherein R$_8$ represents a R$_{11}$ group.

4. The compound according to claim 3, wherein R$_8$ represents a (C$_1$-C$_6$)alkyl group.

5. The compound according to claim 1, selected from among:

| Compound N° | Structures |
|---|---|
| 95 | 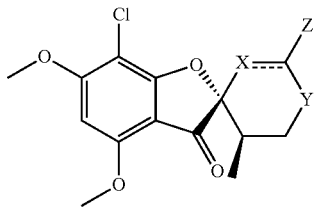 |

| Compound N° | Structures |
|---|---|
| 96 | 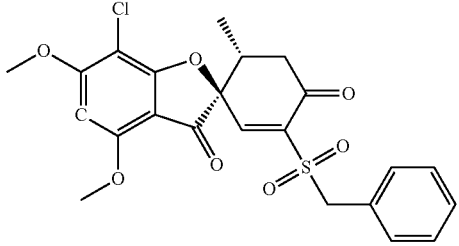 [SMILES: COc1cc(OC)c2c(c1Cl)O[C@@]1(C=C(S(=O)(=O)Cc3ccccc3)C(=O)C[C@H]1C)C2=O] |
| 97 | 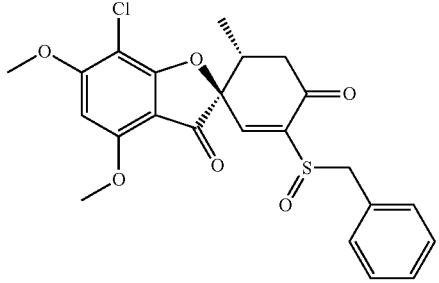 [SMILES: COc1cc(OC)c2c(c1Cl)O[C@@]1(C=C(S(=O)Cc3ccccc3)C(=O)C[C@H]1C)C2=O] |
| Compound N° | Structures |
|---|---|
| 98 | 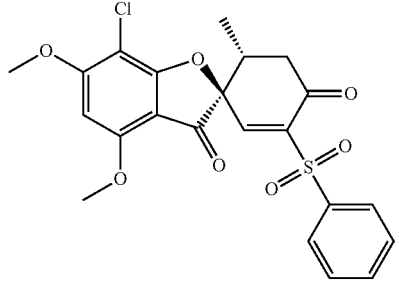 [SMILES: COc1cc(OC)c2c(c1Cl)O[C@@]1(C=C(S(=O)(=O)c3ccccc3)C(=O)C[C@H]1C)C2=O] |
6. A pharmaceutical composition comprising at least one compound according to claim 1 and at least one pharmaceutically acceptable excipient.
* * * * *